United States Patent
Knight et al.

(10) Patent No.: US 6,346,233 B1
(45) Date of Patent: Feb. 12, 2002

(54) COMPOSITION FOR TREATING CANCER VIA LIPOSOMAL AEROSOL FORMULATION CONTAINING TAXOL

(75) Inventors: J. Vernon Knight, Houston; J Clifford Waldrep, The Woodlands; Nadezhda Koshkina; Brian Gilbert, both of Houston, all of TX (US)

(73) Assignee: Research Development Foundation, Carson City, NV (US)

( * ) Notice: Subject to any disclaimer, the term of this patent is extended or adjusted under 35 U.S.C. 154(b) by 0 days.

(21) Appl. No.: 09/617,623

(22) Filed: Jul. 17, 2000

Related U.S. Application Data (62) Division of application No. 08/933,254, filed on Sep. 23, 1997, now Pat. No. 6,090,407.

(51) Int. Cl.$^7$ ............................ A61K 9/12; A61K 9/127
(52) U.S. Cl. ............................ 424/45; 424/46; 424/450
(58) Field of Search ............................ 424/45, 46, 450; 514/725

(56) References Cited

U.S. PATENT DOCUMENTS

| | | | | |
|---|---|---|---|---|
| 5,049,388 A | * | 9/1991 | Knight et al. | |
| 5,736,156 A | * | 4/1998 | Burke | |
| 5,958,378 A | * | 9/1999 | Waldrep et al. | |
| 6,090,407 A | * | 7/2000 | Knight et al. | |

OTHER PUBLICATIONS

Schreier et al. (1993). Journal of Controlled Release, 24:209–223.*

Waldrep et al. (1993). International Journal of Pharmaceutics, 97:205–212.*

* cited by examiner

*Primary Examiner*—Raj Bawa
(74) *Attorney, Agent, or Firm*—Benjamin Aaron Adler (57) ABSTRACT

The small particle liposome or lipid complex aerosol compounds and methods of treatment of the present invention involve lipid- or water soluble anti-cancer drugs incorporated into liposomes or other lipid complexes. The liposomes and complexes are administered in aqueous dispersions from a jet nebulizer to the respiratory tract of an individual. Various anti-cancer drugs may be used, including 20-S-Camptothecin, 9-Nitro-camptothecin, 9-Amino-camptothecin, 10, 11-methylenedioxy-camptothecin and taxol or its derivatives. Administration of these drugs by inhalation provides faster and more efficient absorption of the anticancer drug than does intramuscular administration or oral administration.

5 Claims, 6 Drawing Sheets

COMPOSITION FOR TREATING CANCER VIA LIPOSOMAL AEROSOL FORMULATION CONTAINING TAXOL

This Application is a Divisional of Ser. No. 08/933,254 filed Sep. 23, 1997, U.S. Pat. No. 6,090,407.

BACKGROUND OF THE INVENTION

1. Field of the Invention

The present invention relates generally to the field of pharmacology and cancer treatment. Specifically, the present invention provides formulations and methods for small particle aerosol delivery by inhalation of aqueous dispersions of liposomes carrying anti-cancer drugs to the respiratory tract.

2. Description of the Related Art

Small particle liposome aerosol treatment consists of lipid-soluble or water-soluble anti-cancer drugs incorporated into liposomes, which are administered from aqueous dispersions in a jet nebulizer (see U.S. Pat. No. 5,049,388). Aerosols of 1–3 µm mass median aerodynamic diameter, generated upon nebulization, enable targeted delivery onto surfaces of the respiratory tract. The deposited liposomes subsequently release drug locally within the lung or into the blood circulation with delivery to extra-pulmonary tissue. If the drug is lipid soluble, it will associate with the lipid molecules in a manner specific to the lipid employed, the anti-cancer drug employed and possibly it may be modified further by various soluble constituents which may be included in the suspending aqueous medium. Such soluble constituents may include buffering salts and possibly inositol to enhance the synthesis and secretion of surfactant phospholipid in lung tissue and to minimize respiratory distress already present or that which might result from the aerosol treatment (Hallman, M., et al. Inositol Supplementation in Premature Infants with Respiratory Distress Syndrome, N. Eng. J. Med. 1992 326:1233–1239).

If the drug is water soluble, it may be incorporated by appropriate procedures in aqueous vesicles that exist in concentric spaces between lipid bilayers (lamellae) of the multilamellar liposome. Unilamellar liposomes may be prepared; however, their capacity to entrap either lipid-soluble or water-soluble drugs is diminished since entrapment is restricted to one central vesicle. Additionally, lipid complexes of various sizes can be used.

Nebulization shears liposomes and other lipid complexes to sizes readily discharged from the nozzle of the nebulizer. Liposomes and other lipid complexes up to several microns in diameter are typically sheared to diameters of less than 500 nm, and may be considerably smaller than that depending on the operating characteristics of the nebulizer and other variables. Shearing of water-soluble drugs contained in liposomes or complexes will release appreciable amounts of the water soluble compound, perhaps 50 percent. This is not a contraindication to their use, but it means that two forms of the drug preparation is administered, and the effect includes the therapeutic effect that would be produced by both forms if either form had been given alone. Many other details of liposome aerosol treatment are described in U.S. Pat. No. 5,049,388. Moreover, it is also possible to incorporate more than one drug in a aerosol liposome treatment, either by mixing different drug-containing liposomes, or by using liposomes wherein the drugs have been combined and incorporated together into liposomes.

The prior art is deficient in formulations and methods for small particle aerosol delivery of aqueous dispersions of liposomes or lipid complexes containing anti-cancer drugs. The present invention fulfills this long-standing need and desire in the art.

SUMMARY OF THE INVENTION

The small particle liposome or lipid complex aerosol compounds and methods of treatment of the present invention involve lipid-soluble or water-soluble anti-cancer drugs incorporated into liposomes or other lipid complexes. These drug-carrying lipids then are administered in aqueous dispersions from a jet nebulizer. The present invention demonstrates that speedier and more efficient systemic absorption of drug is actualized after pulmonary administration by aerosol than is actualized by intramuscular or oral administration.

One object of the present invention is to provide a method for treating cancer, comprising the step of delivering, via small particle aerosol, aqueous dispersions of anti-cancer drugs to the respiratory tract of an individual in need of such treatment. Examples of anticancer drugs available for use in this embodiment of the invention include, but are not limited to, 20-S-camptothecin, 9-nitro-camptothecin, 9-amino-camptothecin, 10, 11-methylenedioxy-camptothecin, taxol, taxol-A, mitotane, methotrexate, mercaptopurine, lomustine, interferon, 5-fluorouracil and etopiside. In a more preferred embodiment of this object, the anti-cancer drug is selected from the group consisting of 20-S-camptothecin, 9-nitro-camptothecin, 9-amino-camptothecin, 10, 11-methylenedioxy-camptothecin and taxol. Additionally, in a preferred embodiment of the present objective, the delivery of the anticancer drug is performed by a jet nebulizer.

In another object of the present invention, there is provided a lipid complex or liposome for delivery of anticancer drugs via small particle aerosols comprising an anticancer drug and a lipid, wherein the anticancer drug is at a concentration not exceeding about 10% of the total volume of the preparation and a ratio of the anticancer drug to the suitable solvent is in the range of about 1:1 to about 1:200, preferably in a range of about 1:10 to about 1:100, and most preferably in a range of about 1:10 to about 1:50 (wt:wt) of the preparation. One specific embodiment of this object includes 9-nitro-camptothecin and dilauroylphosphatidylcholine in a ratio of about 1:10 to 1:50 wt:wt; with a particularly preferred embodiment having a 9-nitro-camptothecin and dilauroylphosphatidylcholine of about 1:50 wt:wt. In another embodiment, there is provided a liposome for delivery of anticancer drugs via small particle aerosols comprising Taxol and dilauroylphosphatidylcholine in a ratio of about 1:30 wt:wt.

In yet another embodiment of the present invention, there is provided a liposome produced by the following steps: dissolving a lipid-soluble anticancer drug in a solvent suitable for dissolving the anticancer drug to produce dissolved anticancer drug; adding the dissolved anticancer drug to a dissolved lipid suitable for formulation and delivery of drugs by aerosol to produce a solution, wherein the dissolved anticancer drug is at a concentration not exceeding about 10% of the total volume of the solution and a ratio of the anticancer drug to the lipid is in the range of about 1:1 to about 1:200, preferably in a range of about 1:10 to about 1:100, and most preferably in a range of about 1:10 to about 1:50 (wt:wt) of the solution; and freezing and lyophilizing the solution. At this point, the solution may be stored frozen for later use or dissolved in sterile water for use, producing a suspension, wherein the concentration of the anticancer drug in the sterile water in the suspension is no more than about 5.0 mg/ml.

A preferred embodiment of the above object provides liposomal preparations of 20-S-camptothecin (CPT), 9-nitrocamptothecin (9-NC) and other lipid soluble camptothecin derivatives, produced by the following steps: preparing concentrated stock solutions of said 20-S-camptothecin (CPT), 9-nitrocamptothecin (9-NC) or other-lipid soluble camptothecin derivatives and lipids in compatible solvents; adding appropriate volumes of the 20-S-camptothecin (CPT), 9-nitrocamptothecin (9-NC) or other-lipid soluble camptothecin derivative and lipid concentrated stock solutions to a volume of t-butanol to form a second solution, wherein a concentration of said 20-S-camptothecin (CPT), 9-nitrocamptothecin (9-NC) and other lipid soluble camptothecin derivatives does not exceed 10% of said second solution and wherein a ratio of drug to lipid is in the range of about 1:1 to about 1:200, preferably in a range of about 1:10 to about 1:100, and most preferably in a range of about 1:10 to about 1:50 (wt:wt) in said second solution; freezing said second solution; and lyophilizing said second solution to produce a powder preparation. At this point, the powder preparation may be stored frozen for later use or dissolved in sterile water producing a suspension, wherein a concentration of said anticancer drug in said suspension is no more than about 5 mg/ml.

A more particular embodiment provides liposomes produced by the following steps: preparing a concentrated stock solutions of anticancer drug, for example 100 mg CPT in 1 ml t-butanol or 100 mg 9-NC in DMSO, preparing a stock solution of lipid, for example, 100 mg DLPC in 1 ml butanol; adding appropriate volumes of said concentrated stock solutions to a volume of t-butanol to form a second solution wherein a final volume is about 10 ml, a volume of DMSO, if any, does not exceed 10% (vol:vol) of said final volume, a concentration of anticancer drug does not exceed 10% (wt:wt) of the total volume, and wherein a ratio of drug to lipid is in a range of about 1:1 to about 1:200, preferably in a range of about 1:10 to about 1:100, and most preferably in a range of about 1:10 to about 1:50 (wt:wt); freezing said second solution; and lyophilizing said frozen solution to produce a powder preparation. Tthe powder preparation may then be stored frozen for later use or dissolved in sterile water producing a suspension. Generally, the concentration of the anticancer drug in the suspension is no more than about 5 mg/ml.

Another preferred embodiment of the object above provides a liposome produced by the following steps: mixing taxol with synthetic alpha lecithin: dilauroylphosphatidylcholine; dissolving the taxol-DLPC in t-butanol to produce a preparation; and freezing and lyophilizing the preparation. Liposomes are produced by adding sterile, pure water at a temperature above 25° C., wherein the final concentration of taxol to dilauroylphosphatidylcholine is about 1:1 to about 1:200, preferably in a range of about 1:10 to about 1:100, and most preferably in a range of about 1:25 to about 1:40 (wt:wt). In addition to alpha lecithin, other natural or synthetic lecithins may be used, including but not limited to egg yolk phosphatidylcholine, hydrogenated soybean phosphatidylcholine, dimyristophosphatidylcholine, diolyeolyl-dipalmitoyleolylphospha-tidylcholine and dipalmitoyl phosphatidylcholine.

The efficiency of incorporation of 9-NC and other camptothecin derivatives and anticancer drugs into liposomes can be tested by layering an aqueous dispersion of lyophilized drug-liposome preparation over a Percoll™ gradient and centrifuging. Unincorporated drug collects at the bottom of the tube, but drug incorporated into liposomes collects at the interface between the Percoll gradient and the water phase.

One qualitative test of incorporation efficiency is the observation of drug crystals when the dispersion of drug-liposomes are examined by microscopy under polarized light. Other methods are also available, for example, analytical HPLC methods can be used to quantitatively assess non-encapsulated, crystalized drug.

Other and further aspects, features, and advantages of the present invention will be apparent from the following description of the presently preferred embodiments of the invention. These embodiments are given for the purpose of disclosure.

BRIEF DESCRIPTION OF THE DRAWINGS

The appended drawings have been included herein so that the above-recited features, advantages and objects of the invention will become clear and can be understood in detail. These drawings form a part of the specification. It is to be noted, however, that the appended drawings illustrate preferred embodiments of the invention and should not be considered to limit the scope of the invention.

DETAILED DESCRIPTION OF THE INVENTION

The following definitions are provided. Terms not specifically defined are meant to interpreted as is customary in the art.

As used herein, the term "aerosols" refers to dispersions in air of solid or liquid particles, of fine enough particle size and consequent low settling velocities to have relative airborne stability (See Knight, V., Viral and Mycoplasmal Infections of the Respiratory Tract. 1973, Lea and Febiger, Phila. Pa., pp. 2). "Liposome aerosols" consist of aqueous droplets within which are dispersed one or more particles of liposomes or liposomes containing one or more medications intended for delivery to the respiratory tract of man or animals (Knight, V. and Waldrep, J. C. Liposome Aerosol for Delivery of Asthma Medications; see also In Kay, B., Allergy and Allergic Diseases, 1997, Blackwell Publications, Oxford, England, Vol. I pp. 730–741). The size of the aerosol droplets defined for this application are those described in U.S. Pat. No. 5,049,338, namely mass median aerodynamic diameter (MMAD) of 1–3 $\mu$m with a geometric standard deviation of about 1.8–2.2. However, with low concentrations of 9-NC and possibly other camptothecin derivatives, the MMAD may be less than 1 $\mu$m, such as 0.8 $\mu$m. Based on the studies disclosed by the present invention, the liposomes may constitute substantially all of the volume of the droplet when it has equilibrated to ambient relative humidity.

As used herein, the "Weibel Lung Model" refers to a classification of the structure of the human lungs that recognizes 23 consecutive branchings of the airways of humans. The trachea is labeled 0, bronchi and bronchioles extend through branches 16. These portions of the airways contain ciliated epithelium and mucus glands. Together they constitute the mucociliary blanket. Branchings 17–23 compose the alveolar portion of the lung and do not have a mucociliary blanket. Thus, particles deposited here are not carried up the airway to be swallowed.

As used herein, the terms "20-S-camptothecin" or "CPT" refers to a plant alkaloid with anti-cancer properties.

As used herein, the terms "9-nitro-camptothecin" or "9-NC", "9-amino-camptothecin" or "9-AC," and "10, 11-methylenedioxy-camptothecin" or "MDC" refer to active anti-cancer drugs derived from 20-S-camptothecin that are insoluble in water but are soluble in certain lipid solvents.

As used herein, the terms "dilauroylphosphatidylcholine" or "DLPC" is a lipid used to formulate liposomes.

The present invention is directed to a method for treating cancer, comprising the step of delivering, via small particle aerosol, aqueous dispersions of anti-cancer drugs to the respiratory tract of an individual in need of such treatment. In a preferred embodiment of this object, the anti-cancer drug is selected from the group consisting of 20-S-camptothecin, 9-nitro-camptothecin, 9-amino-camptothecin and 10, 11-methylenedioxy-camptothecin. Additionally, in a preferred embodiment of the present objective, the delivery of the anticancer drug is performed by a jet nebulizer.

Additionally, there is a liposome for delivery of anticancer drugs via small particle aerosols comprising an anticancer drug and a lipid, wherein the anticancer drug is at a concentration not exceeding about 10% of the total volume of the preparation and a ratio of the anticancer drug to the suitable solvent is in the range of about 1:1 to about 1:200, preferably in a range of about 1:10 to about 1:100, and most preferably in a range of about 1:10 to about 1:50 (wt:wt) of the preparation. One specific embodiment of this object includes 9-nitro-camptothecin and dilauroylphosphatidylcholine in a ratio of about 1:10 to 1:50 wt:wt; with a particularly preferred embodiment having a 9-nitro-camptothecin and dilauroyl-phosphatidylcholine of about 1:50 wt:wt.

Taxol is another anti-cancer drug that is lipid soluble and is incorporated easily into a liposome formulation. The optimal ratio for taxol and dilauroylphosphatidylcholine is a ratio of about 1:1 to about 1:200, preferably in a range of about 1:10 to about 1:100, and more preferably in a range of about 1:25 to about 1:40 (wt:wt). A most preferred embodiment provides a taxol to DLPC ratio of about 1:30. Taxol is directly dissolved in t-butanol without use of DMSO as is used for some camptothecins. The Taxol liposomal preparation is otherwise similar to that of the camptothecins.

Further, the present invention is directed to liposomes for delivery of anticancer drugs via small particle aerosols produced by the following steps: dissolving a lipid-soluble anticancer drug in a solvent suitable for dissolving the anticancer drug to produce dissolved anticancer drug; adding the dissolved anticancer drug to a dissolved lipid suitable for formulation and delivery of drugs by aerosol to produce a solution, wherein the dissolved anticancer drug is at a concentration not exceeding about 10% of the total volume of the solution and a ratio of the anticancer drug to the suitable solvent is in the range of about 1:1 to about 1:200 of the solution; and freezing and lyophilizing the solution. At this point, the solution may be stored frozen for later use or dissolved in sterile water to produce a suspension, wherein the concentration of the anticancer drug in the sterile water in the suspension is no more than about 5.0 mg/ml. A particular embodiment of the present invention provides a liposome produced by the following steps: dissolving a lipid-soluble anticancer drug selected from the group of 20-S-camptothecin, 9-nitro-camptothecin, 9-amino-camptothecin and 10, 11-methylenedioxy-camptothecin in 100% DMSO to produce dissolved anticancer drug; and adding said dissolved anticancer drug to dilauroylphosphatidylcholine dissolved in t-butanol to produce a solution, wherein the dissolved anticancer drug is at a concentration not exceeding about 5% of the total volume of the solution and the ratio of anticancer drug to dilauroylphosphatidylcholine is about 1:50 in the solution. The solution is frozen and lyophilized overnight. For use, the lyophilized solution is suspended in appropriate volumes of sterile, distilled water. In addition, other methods of liposome preparation known in the art may be utilized, for example, rotary evaporation can be used instead of lyophilization.

9-NC-DLPC aerosol is prepared by first dissolving the drug in DMSO; to do so, heating to 50–60° C. may be required. This solution is added to a larger volume of t-butanol, such that the DMSO solution does not exceed 5–10% of the total t-butanol and DMSO volume combined. The organic solvents DMSO and t-butanol are evaporated from the solution on liquid nitrogen resulting in a slightly yellow powder. For use, distilled sterile water is added to the vials containing the drug at the appropriate concentration and added to the reservoir of the nebulizer. The Aerotech II™ nebulizer CIS-USA, Inc., Bedford Mass. is currently employed, but other nebulizers with similar aerosol-generating properties may be used.

A particular embodiment of the present invention is directed to a liposome produced by the following steps: mixing taxol with synthetic alpha lecithin: dilauroylphosphatidylcholine; dissolving the taxol-DLPC in t-butanol to produce a solution; and freezing and lyophilizing the solution. Liposomes are produced by adding sterile, pure water at a temperature above 25° C., wherein the final concentration of taxol to dilauroylphosphatidylcholine is about 1:1 to about 1:200, preferably in a range of about 1:10 to about 1:100, and more preferably in a range of about 1:25 to about 1:40 (wt:wt).

It is contemplated specifically that the pharmaceutical compositions of the present invention be used for aerosol delivery of aqueous dispersions of liposomes carrying anticancer drugs to the respiratory tract. A person having ordinary skill in this art would readily be able to determine, without undue experimentation, the appropriate dosages of these aerosol formulations. When used in vivo for therapy, the aerosol formulations of the present invention are administered to the patient in therapeutically effective amounts; i.e., amounts that eliminate or reduce the tumor burden. As with all pharmaceuticals, the dose and dosage regimen will depend upon the nature of the cancer (primary or metastatic), the characteristics of the particular drug (e.g., its therapeutic index), the patient, the patient's history and other factors. The amount of aerosol formulation administered will typically be in the range of about 8 µg/kg of patient weight/day to about 100 µg/kg of patient weight/day for 9-NC. Again, dose and dosage regimen will vary depending on a number of factors known to those skilled in the art. See Remington's Pharmaceutical Science, 17th Ed. (1990) Mark Publishing Co., Easton, Pa.; and *Goodman and Gilman's: The Pharmacological Basis of Therapeutics* 8th Ed (1990) Pergamon Press.

The small particle liposome aerosol compounds and methods of treatment of the present invention involve lipid- or water-soluble anti-cancer drugs incorporated into liposomes. The liposomes are administered in aqueous dispersions from a jet nebulizer. Various anti-cancer drugs may be used, including 20-S-camptothecin, 9-nitro-camptothecin, 9-amino-camptothecin, 10, 11-methylenedioxy-camptothecin and taxol.

The following examples are given for the purpose of illustrating various embodiments of the invention and are not meant to limit the present invention in any fashion:

EXAMPLE 1
Anti-cancer Drugs CPT and its 9-NC Derivative

Representative of the anti-cancer drugs of the present invention are 20-S-camptothecin and its 9-NC derivative. Other camptothecins such as 9-AC and 10, 11-MDC, as well as other anticancer formulations known in the art, also possess properties suitable for use. All these anti-cancer drugs may be used in liposome formulations.

Table 1 shows a comparison of blood or plasma concentrations of 9-NC and the time of peak concentrations following oral administration to humans, dogs and mice. (Hinz, H. R., et. al. Pharmacokinetics of the in vivo and in vitro conversion of 9-Nitro 20-(S)-camptothecin to 9-Amino-20-(S)-camptothecin in Humans, Dogs and Mice. *Cancer Research* 1994 54:3096–3100). Single oral doses ranged from 0.1 to 1.0 mg/kg for humans and dogs and were 4.1 mg/kg for mice. There may be some differences in pharmacokinetics between CPT and 9-NC, but it is a reasonable possibility that the foregoing differences are predictive of the properties of both agents.

TABLE 1

Comparison of 9-NC concentrations in blood or plasma following single oral, intranasal or aerosol dosage

| | | Blood or plasma concentration | Time of maximum concentration |
|---|---|---|---|
| | Oral dose (Single doses) | | |
| Human | 0.1 mg/kg (7 mg/dose) | 483 ng/ml | 3.4 h (T½ = 2.5 h) |
| | 1.0 mg/kg (70 mg/dose) | 1247 ng/ml | 5.3 h (T½ = 4.9 h) |

TABLE 1-continued

Comparison of 9-NC concentrations in blood or plasma following single oral, intranasal or aerosol dosage

| | | Blood or plasma concentration | Time of maximum concentration |
|---|---|---|---|
| Dog | 1.0 mg/kg (10 mg/dose) | 19.1 ng/ml | 0.7 h (T½ = 6.4 h) |
| Mouse | 4.1 mg/kg (0.124 mg/dose) | 732 ng/ml | 6 min (T½ = 10 h) |
| | *Intranasal | | |
| Mouse | 233 µg/kg (7 µg/mouse) | 213 ng/ml | end of instillation |
| | *Inhaled in liposome aerosol (30 min) | | |
| Mouse | 16.2 µg/kg (486 ng/mouse) | 13.9 ng/ml | end of aerosolization |

*Intranasal and aerosol results from Baylor Aerosol Labratory, the others from Hinz, H.R. (see text for reference)

Table 2 describes the method of calculating aerosol dosage in the mouse, and this is the basis for determining dosages cited in Table 1. Much of the inhaled drug is deposited in the nasopharynx of the mouse because of the complex nose structure of rodents. Similarly, nasal instillation leads to high nasopharyngeal deposition. Material deposited here is promptly transported to the esophageal orifice and swallowed. About 10–15 percent of the inhaled aerosol dose, however, will penetrate to the peripheral lungs.

In humans with mouth breathing, only small amounts of the aerosol particles will deposit in the mouth and virtually none will deposit in the nasopharynx. Material deposited in the central airways is returned to the pharynx by mucociliary action where it is swallowed. In the case of primary lung tumors which often occur at bronchial bifurcations, drug will deposit on tumor surfaces and be adsorbed directly into the tumor mass. Material deposited beyond the 16th Weibel generation, which is beyond the ciliated epithelium, will not be moved upward; thus, in tumors within the peripheral lung parenchyma, the drug will deposit in adjacent areas and be absorbed directly into the tumor mass. In addition, a major advantage of the present invention is that drug deposited beyond the ciliated epithelium is picked up by capillaries in the interstitial space and the lymphatics of the lungs and will enter the circulation.

TABLE 2

Calculation of deposited doses of 9-NC in different species when administered by aerosol NEBULIZER: AeroTech II; 10 L/min; Measured 1.7% efficiency
RESERVOIR: 9-Nitrocamptothecin (9NC)-DLPC liposomes: 100, 500 or 1,000 µg 9NC/mL and 1:50 (w/w) mg DLPC/mL Dose Calculation

| Species | Drug | MMAD | 9NC in Resv (µg/mL) | 9NC in Aerosol (µg/L) | Body Wt (kg) | Rx Time (min/day) | K* | Drug Dose (µg/kg/min) | Total Drug (µg/kg/day) | (µg/day) | Resp Secr (µg/mL)** | Weibel Generations: 0–16 (µg/mL)*** | Weibel Generations: 17–23 (µg/mL)*** |
|---|---|---|---|---|---|---|---|---|---|---|---|---|---|
| Human [adult] | 9NC | 0.8 | 100 | 1.8 | 70 | 15 | 0.076 | 0.14 | 2.0 | 142 | 0.68 | 1.4 | 5.8 |
| Human [adult] | 9NC | 0.8 | 100 | 1.8 | 70 | 30 | 0.076 | 0.14 | 4.1 | 284 | 1.35 | 2.7 | 11.7 |
| Human [adult] | 9NC | 1.2 | 500 | 8.5 | 70 | 15 | 0.076 | 0.64 | 9.6 | 675 | 3.21 | 6.5 | 27.7 |
| Human [adult] | 9NC | 1.2 | 500 | 8.5 | 70 | 30 | 0.076 | 0.64 | 19.3 | 1,353 | 6.44 | 13.0 | 55.5 |
| Human [adult] | 9NC | 1.5 | 1,000 | 15.9 | 70 | 15 | 0.076 | 1.20 | 18.0 | 1,259 | 6.00 | 12.1 | 51.6 |
| Human [adult] | 9NC | 1.5 | 1,000 | 15.9 | 70 | 30 | 0.076 | 1.20 | 36.0 | 2,518 | 11.99 | 24.2 | 103.3 |
| Dog | 9NC | 1.2 | 500 | 8.5 | 30 | 15 | 0.100 | 0.85 | 12.8 | 383 | 4.26 | 8.6 | 36.7 |
| Dog | 9NC | 1.2 | 500 | 8.5 | 30 | 30 | 0.100 | 0.85 | 25.6 | 767 | 8.52 | 17.2 | 73.4 |

TABLE 2-continued

Calculation of deposited doses of 9-NC in different species when administered by aerosol

| Cotton Rat | 9NC | 1.2 | 500   | 8.5  | 0.075 | 30  | 0.350 | 2.98 | 89.5  | 6.71  | 29.8  |
|------------|-----|-----|-------|------|-------|-----|-------|------|-------|-------|-------|
| Cotton Rat | 9NC | 1.2 | 500   | 8.5  | 0.075 | 60  | 0.350 | 2.98 | 178.9 | 13.42 | 59.6  |
| Cotton Rat | 9NC | 1.2 | 500   | 8.5  | 0.068 | 30  | 0.350 | 2.98 | 89.5  | 6.08  | 29.8  |
| Mouse      | 9NC | 0.8 | 100   | 1.8  | 0.030 | 15  | 0.300 | 0.54 | 8.1   | 0.24  | 2.7   |
| Mouse      | 9NC | 0.8 | 100   | 1.8  | 0.030 | 30  | 0.300 | 0.54 | 16.1  | 0.48  | 5.4   |
| Mouse      | 9NC | 1.2 | 500   | 8.5  | 0.030 | 15  | 0.300 | 2.55 | 38.3  | 1.15  | 12.8  |
| Mouse      | 9NC | 1.2 | 500   | 8.5  | 0.030 | 30  | 0.300 | 2.56 | 76.7  | 2.30  | 25.6  |
| Mouse      | 9NC | 1.2 | 500   | 8.5  | 0.030 | 60  | 0.300 | 2.56 | 153.4 | 4.60  | 51.1  |
| Mouse      | 9NC | 1.2 | 500   | 8.5  | 0.030 | 120 | 0.300 | 2.56 | 306.7 | 9.20  | 102.2 |
| Mouse      | 9NC | 1.5 | 1,000 | 15.9 | 0.030 | 15  | 0.300 | 4.76 | 71.4  | 2.14  | 23.8  |
| Mouse      | 9NC | 1.5 | 1,000 | 15.9 | 0.030 | 30  | 0.300 | 4.77 | 143.1 | 4.29  | 47.7  |

*K(human/adult): 0.108 L-min/kg × 0.7; Assuming Nose and mouth breathing, Mouth-only = ½
K(cotton rat): 0.7 L-min/kg × 0.5
K(mouse): 1 L-min/kg × 0.3
K(dog, golden): 0.2 L-min/kg × 0.5
**Estimated Peak after each treatment: secretion volume 1 mL/kg
***Based on data from Patton (3570) and Philadelphia info; Mouth-only breathing in man Table 3 shows the tissue distribution of CPT following 15 minutes of nebulization in DLPC liposome aerosol. The deposited dose was calculated to be 486 ng per mouse. The mean concentrations in lungs and liver were similar with smaller concentrations in the other sites examined. Table 4 shows tissue distributions over a period of one hour following intranasal instillation of 7 µg per mouse (233 µg/kg). Drug was cleared promptly from the lungs so that by 15 minutes after stopping nebulization only negligible amounts of drug were present in the lungs. Liver, kidney and spleen had substantial amounts of drug initially which gradually diminished through the one hour of study. Interestingly, blood concentrations were the least throughout the study. These studies indicate substantial immediate deposition of drug in the lungs with rapid clearance to the viscera. The amount of drug contributed by absorption from swallowed drug is uncertain.

TABLE 3

Tissue distribution of CPT following 15 minutes inhalation of CPT liposome aerosol

| Animal | Organ | CPT (ng/gm) tissue |
|--------|-------|--------------------|
| 1 | Lung | 52.0 |
|   | Liver | 44.3 |
|   | Spleen | 12.0 |
|   | Kidney | 29.3 |
|   | Blood | 7.1 |
| 2 | Lung | 48.0 |
|   | Liver | 44.3 |
|   | Spleen | 16.4 |
|   | Kidney | 21.8 |
|   | Blood | 8.3 |
| 3 | Lung | 27.0 |
|   | Liver | 21.9 |
|   | Spleen | 11.4 |
|   | Kidney | 18.0 |
|   | Blood | 22.6 |
| 4 | Lung | 77.5 |
|   | Liver | 178.0 |
|   | Spleen | 25.0 |
|   | Kidney | 50.0 |
|   | Blood | 17.7 |
| MEAN (±SD) CPT (ng/gm tissue) | | |
|   | Lung | 51.1 ± 20.7 |
|   | Liver | 72.1 ± 71.4 |
|   | Spleen | 16.2 ± 6.3 |

TABLE 3-continued

Tissue distribution of CPT following 15 minutes inhalation of CPT liposome aerosol

| Animal | Organ | CPT (ng/gm) tissue |
|--------|-------|--------------------|
|  | Kidney | 29.8 ± 14.3 |
|  | Blood  | 13.9 ± 7.5  |

The CPT concentration in the liposomal preparation in the nebulizer was 0.2 mg/ml aerosol was generated with an Aerotech II nebulizer operating at a flow rate of 10 L/min.

TABLE 4

Time dependent organ distribution of CPT after intranasal administration

| | ng/gm of tissue Time (minutes) | | | |
|---|---|---|---|---|
| Organ | 0 | 15 | 30 | 60 |
| Lung   | 1287 ± 657 | 19 ± 3   | 36 ± 23 | 7 ± 3  |
| Liver  | 651 ± 418  | 255 ± 101 | 66 ± 17 | 34 ± 7 |
| Kidney | 542 ± 174  | 190 ± 57 | 49 ± 13 | 24 ± 21 |
| Spleen | 351 ± 137  | 84 ± 32  | 21 ± 8  | 7 ± 2  |
| Blood  | 213 ± 19   | 53 ± 20  | 8 ± 3   | 4 ± 2  |

Remarks

CPT was administered in liposomal formulation prepared with DLPC with initial drug concentration 0.2 mg/ml.

35 µL of suspension was installed to each animal (group of 3 animals was treated for each time point).

Table 5 shows the distribution of drug in blood and viscera following intramuscular injection of CPT. Drug disappeared very slowly from the site of intramuscular injection in the first 12 hours, with only very small concentrations detected in the liver and virtually no drug present at other sites. Concentrations in the blood were negligible throughout the study. The dose administered was the same as that given by intranasal instillation. These findings indicate a speedier and more efficient systemic absorption of drug after pulmonary administration of drug than by the intramuscular route. It is likely that deposition in organs and vascular spaces will increase the opportunity for exposure to albumin molecules and degradation to the carboxyl form of the drug.

TABLE 5

Time dependent organ distribution of CPT after intramuscular administration

| | ng/gm tissue Time (minutes) | | | |
|---|---|---|---|---|
| Organ | 0 | 30 | 60 | 1200 |
| Lung | 2 ± 1 | 4 ± 2 | 3 ± 3 | 4 ± 3 |
| Liver | 3 ± 1 | 87 ± 74 | 136 ± 107 | 126 ± 116 |
| Spleen | 2 ± 1 | 18 ± 9 | 11 ± 5 | 5 ± 1 |
| Kidney | 2 ± 0 | 40 ± 14 | 26 ± 7 | 15 ± 5 |
| Blood | 2 ± 1 | 12 ± 5 | 8 ± 1 | 4 ± 1 |
| Site of inj. | 6918 ± 265 | 4309 ± 1548 | 4609 ± 1412 | 1544 ± 751 |

Remarks

CPT initial stock 5 mg/ml in DMSO was suspended in saline (1.4 µL stock+48.6 µL saline) and total 50 µL of suspension was injected i.m. in each mice.

Group of 3 animals was treated for each time point.

EXAMPLE 2

Stability of Liposomes Consisting of DLPC and 9-AC

Table 6 shows the stability of liposomes with fixed weight ratio of 9-NC and DLPC of 1:50 (w/w) but with increasing concentrations of constituents from 0.1 mg/ml to 1.0 mg/ml of drug. The samples were tested under various conditions after vortexing, but before start of nebulization, after nebulization for 1.5 to 2 minutes (sample taken from the fluid in the reservoir of the nebulizer) and from the aerosol that was collected in an all-glass impinger (All-Glass Impinger, Ace Glass Co., Vineland N.J.).

TABLE 6

Liposome particle size and drug crystal formation in preparation of 9-NC DLPC liposome formulations

| Concentration (mg/ml) | | | Liposome particle | Crystals presence |
|---|---|---|---|---|
| 9NC | DLPC | Sample | size, nm | (visual estimation) |
| 0.1 | 5.0 | 1 | 8006 | − |
| | | 2 | 798 | + |
| | | 3 | 332 | − |
| 0.2 | 10.0 | 1 | 6201 | − |
| | | 2 | 434 | + |
| | | 3 | 812 | − |
| 1.0 | 50.0 | 1 | 5448 | ++ |
| | | 2 | 718 | ++ |
| | | 3 | 816 | + |

1 sample was tested after vortexing
2 samples was taken from nebulizer reservoir after 1.5 to 2 minutes of aerosolization
3 sample was from aerosol collected in an AGI containing water The most stable preparation was the one with lowest concentration of constituents. A few crystals appeared in the reservoir following nebulization. Nebulization caused a tenfold reduction in the diameter of the liposome particles, due to the shear forces associated with nebulization. There was further reduction in the diameter of liposome particles recovered from the aerosol. This finding is consistent with selection of smaller particles for discharge in aerosol. The lack of crystals suggests that crystals may not nebulize as readily as liposomes. With larger dosages of liposomes, size reduction following nebulization occurred, but particles recovered from aerosol were not reduced in size compared to particles that had been cycled in the reservoir of the nebulizer.

EXAMPLE 3

Kinetics of Lactone Ring Opening

The anti-tumor activity of several of the camptothecins are diminished following dissolution in aqueous media. This is due to a hydrolyzable alpha-hydroxy lactone ring (ring E). The change results from acyl cleavage yielding the biologically inactive carboxylate form of the molecule. The lactone ring form of the drug is sheltered in liposomes (Burke, T. G., Biochemistry 1993 32:5352–5364), but the carboxyl form of the drug has high affinity for human serum albumin. This leads to rapid conversion of lactone to carboxylate in the presence of human serum albumin, and thus to loss of anti-cancer activity. Deposition within the lungs on alveolar surfaces where there is little albumin and/or interaction with constituents of the liposomes is clearly a factor in preserving the anti-cancer effect of 9-NC.

EXAMPLE 4

Effect of 9-NC on Growth of Human Breast Cancer Explants in Mice

Figure 1:
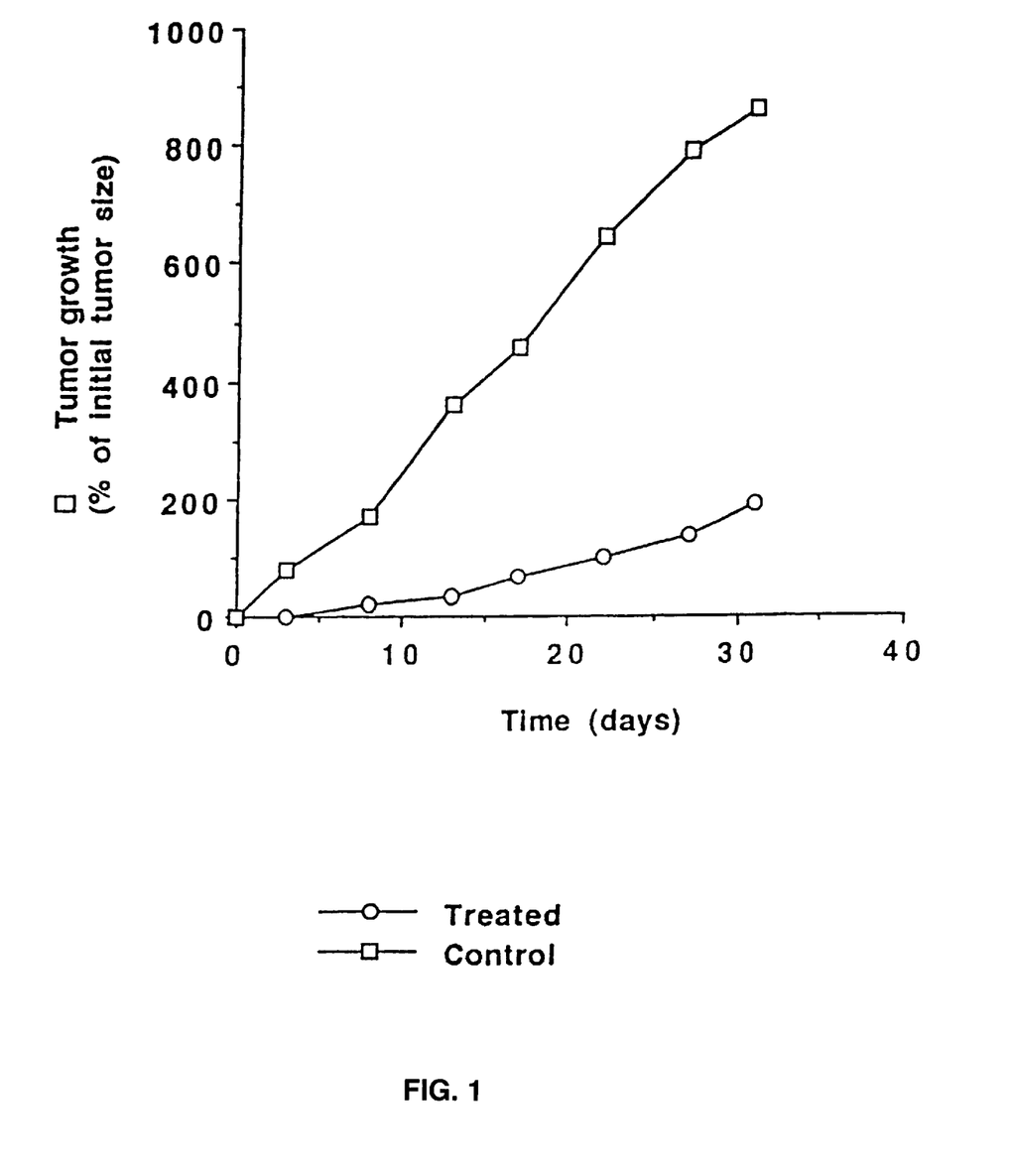
FIG. 1: shows the effect of treatment with 9-NC-DLPC liposome aerosol on xenografted human breast cancer in nude mice.
Figure 2:
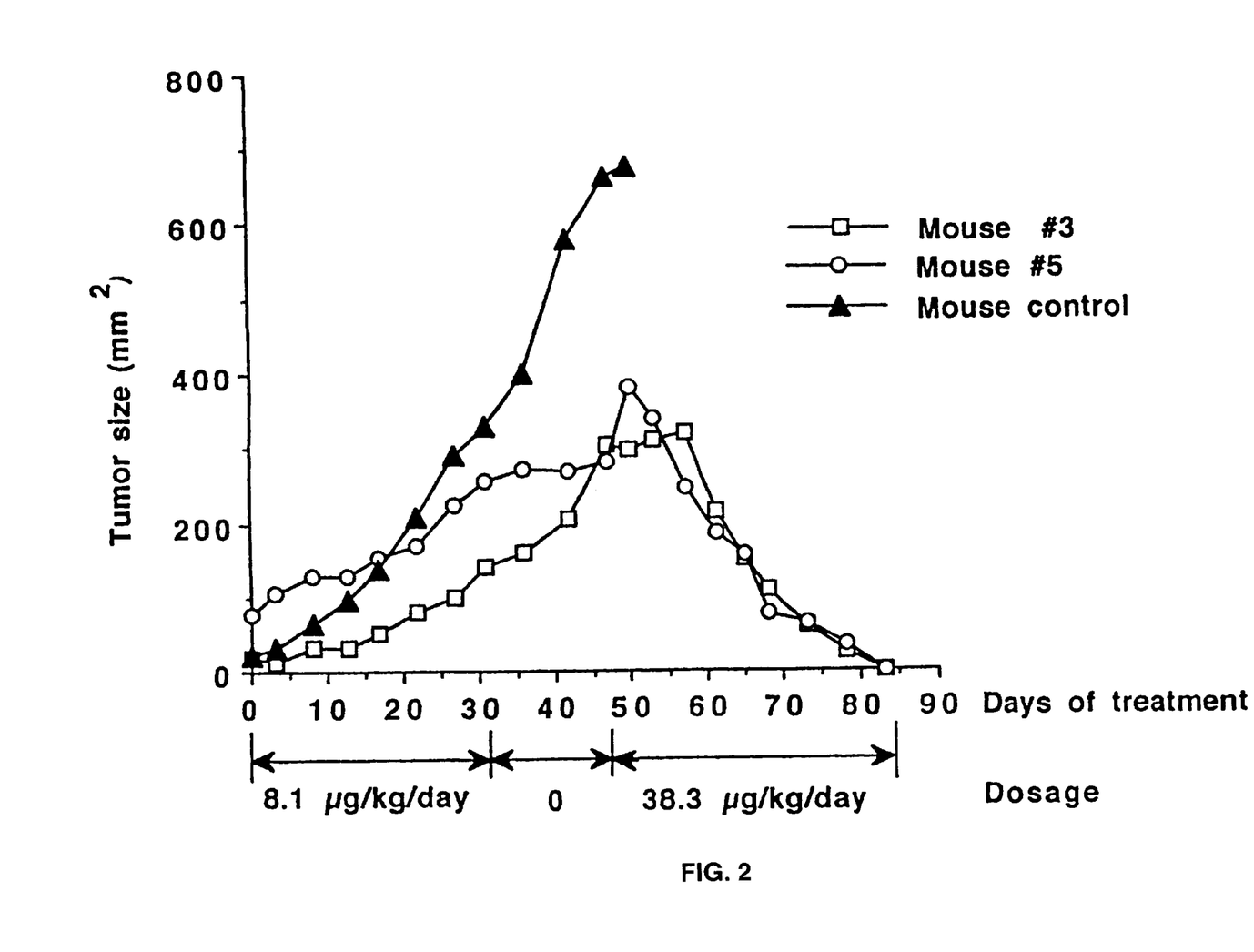
FIG. 2: shows the effect of further treatment with 9-NC-DLPC liposome aerosol in mice selected from FIG. 1.
Figure 3:
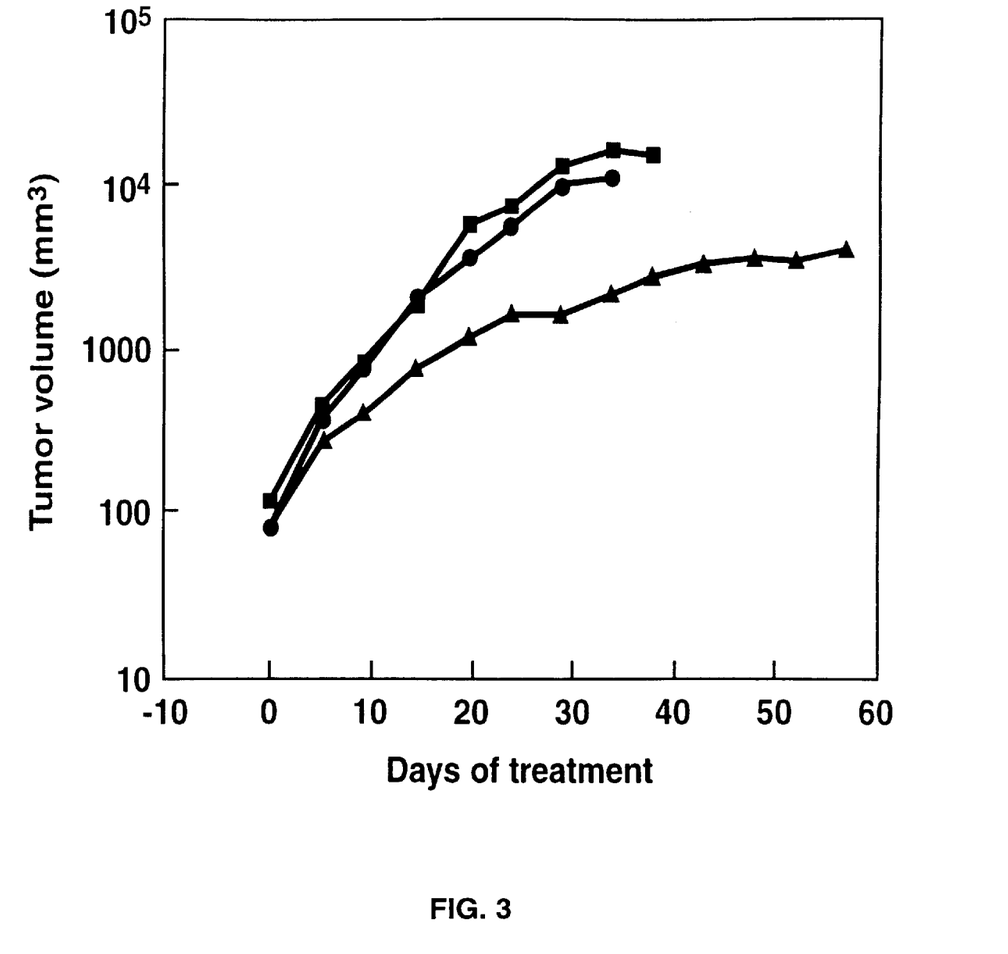
FIG. 3: shows the effect of treatment with 9-NC-DLPC liposome aerosol on xenografted human colon cancer (Squires) in nude mice.

FIG. 1 shows growth in the area of subcutaneous breast cancer xenografts during treatment with 9-NC-DLPC liposome aerosol. There were six 9-NC treated and 5 control mice. Treatments were given 15 minutes daily, five days per week. The dose was 8.1 µg/kg per day. The deposited dose in the respiratory tract of each mouse was estimated to be 234 ng per day. The data on tumor size was normalized and the divergence of tumor size (% initial tumor growth) in the two groups was highly significant by day 17 of treatment ($P<0.011$). After this time, control mice were sacrificed because of the presence of large necrotic tumor masses. FIG. 2 shows the course of events with two treated mice which were subsequently followed with higher doses of drug, following a period of 16 days without treatment. A few days following restart of treatment with a five-fold increase in the dose of 9-NC liposome aerosol, the size of tumors in the treated animals diminished rapidly, and were no longer visible by the 85th day after start of treatment.

EXAMPLE 5

Effect of 9-NC on Human ColoRectal Cancer Xenografts in Nude Mice

A similar study was performed in nude mice with human colon carcinoma xenografts and is shown in FIG. 3. There were 15 treated and 20 control mice. Ten controls received empty DLPC liposomes and 10 received no treatment. Control animals who received no treatment or DLPC only showed a consistent and rapid increase in tumor size until they were sacrificed on day 36. The overall rate of tumor growth was 7 to 11 times greater in control than in 9-NC-treated mice. The treated animals were divided into two groups of 10 each. One group received 77 μg/kg/daily, five days per week throughout the entire experiment. The other received 77 μg/kg per day five days per week until day 35 when the dose was increased to 153 μg/kg per day five days per week until day 46 when it was increased to 307 μg/kg on the same schedule until day 61. There was slightly less increase in tumor size in the group receiving the higher dose, but the differences were not statistically significant, and the data are combined in the figure. Four mice in the DLPC treatment group were sacrificed because of large tumors or tumor necrosis before day 61, and six mice in the no treatment group were sacrificed for the same reasons before day 61. In the treatment group five mice were sacrificed because of tumor necrosis or emaciation before day 61. The emaciated mice were in the high dose group, suggesting drug toxicity. One additional treated mouse was sacrificed because of rectal prolapse. Based on these findings of reduced rate of tumor growth, day 28, (P<0.007, Student t test, 2 tailed) and reduced mortality there is an unequivocal therapeutic effect of 9-NC treatment (P<0.002~chi square test).

EXAMPLE 6

Effect of 9-NC on Human Lung Carcinoma Xenografts in Nude Mice

Additionally, studies were performed on the effect of treatment with 9-NC-DLPC via liposome aerosol or via oral administration on the growth of human lung cancer xenografts (Spark) in nude mice as measured by tumor volume. Treatment was initiated about two weeks after tumor implantation. Control animals showed a rapid increase in volume of tumors. Animals who received oral dosage with the liposome drug aqueous suspension in doses of 100 µg/kg/day—more than twice the aerosol dosage—did not respond to treatment. See FIG. 4.

Figure 4:
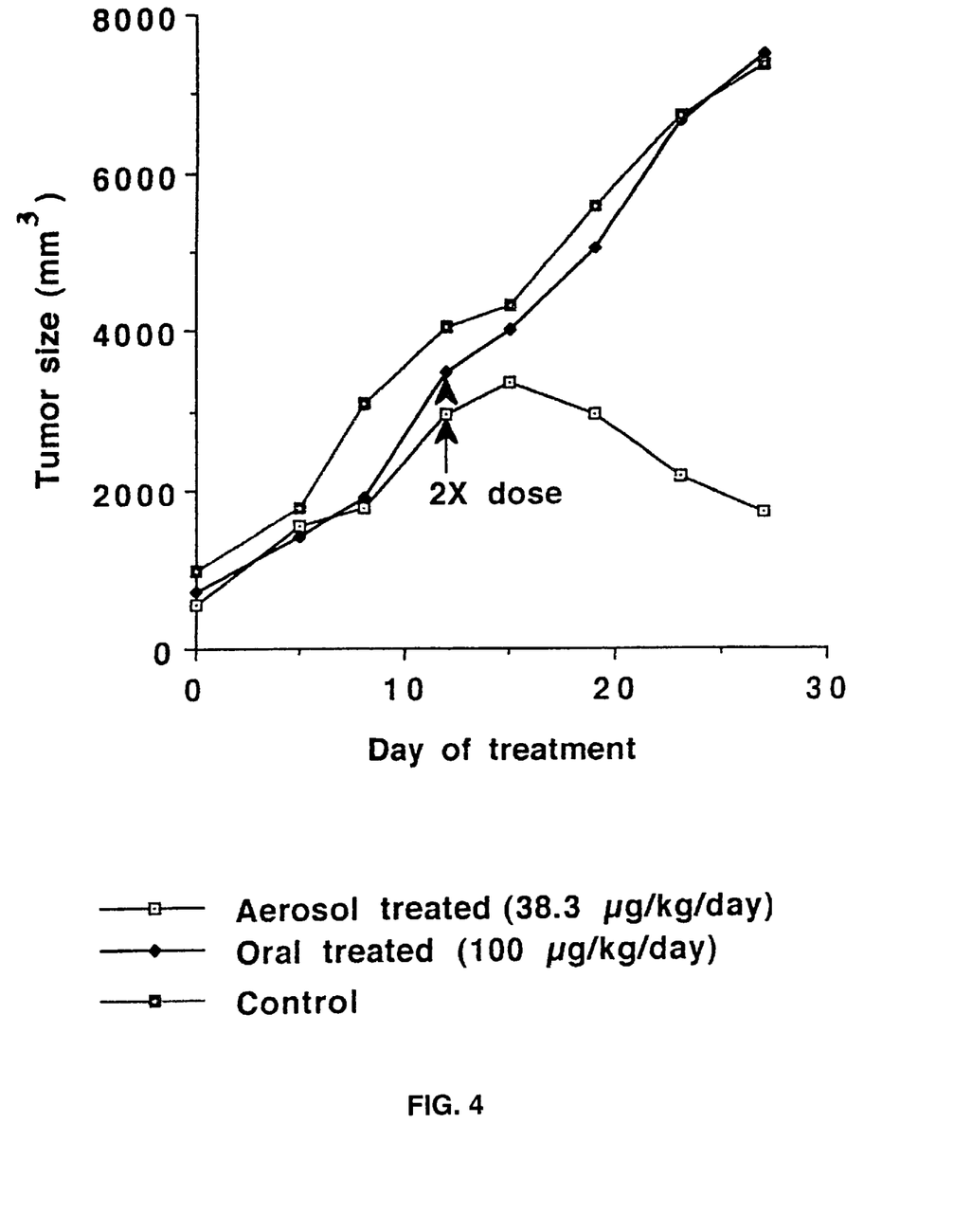
FIG. 4: shows the effect of treatment with 9-NC-DLPC by liposome aerosol or by oral administration on the growth of human lung cancer xenografts (Spark) in nude mice as measured by tumor volume.

Both aerosol and oral doses were doubled on day 13. The increased dosage was followed by decrease in the size of tumors treated with aerosol, but there was no decrease in size of tumors in mice given oral treatment. Thus, despite the fact that half or more of aerosol dosage administered to mice is deposited in the nose, head, trachea and upper bronchi and is promptly carried by the mucociliary system to the esophagus where it is swallowed, the fraction of inhaled drug that is deposited in the lung is principally responsible for the effect on tumor growth.

The most likely explanation of the clear efficiency of aerosol delivery is the rapid entry of the drug to the circulation where it is returned to the left heart, and then to the aorta and peripheral circulation. Thus, the drug would reach the tumors on "first pass" without having passed through the liver, which would remove large amounts of drug from blood.

EXAMPLE 7

Animal Models

Nude Mice: Swiss immunodeficient nude mice of the NIH-1 high fertility strain, bred and housed at the Stehlin Institute were used for these experiments (Giovella, B. C., et al., Complete Growth Inhibition of Human Cancer Xenografts in Nude Mice by Treatment with 20-(S)-Camptothecin, *Cancer Research* 1991 51:3052–3055).

Human Cancer Xenografts: Human heterotransplants were established in nude mice. For an implant, approximately 50 mg of wet weight of finely minced tumor in 0.5 ml of Eagles minimum essential medium was injected under the skin over the right dorsal chest region. The animals were started on treatment with the experimental drug about 10 days after implantation of tumors. Tumors of breast cancers were measured in two dimensions (i.e. area) with calipers, while colon cancers were measured in three dimensions (i.e. volume) with calipers.

EXAMPLE 8

Camptothecin Liposome Aerosol Formulation and Administration

CPT and 9-nitrocamptothecin were provided by Dr. Beppino Giovanella of the Stehlin Institute, Houston, Tex. DLPC was obtained from Avanti Polar Lipids, Pelham, Ala. Aerotech II nebulizers were obtained from Cis-USA, Inc., Bedford, Mass.

For formulation of liposomes, 9-NC (100 mg/ml) or CPT (10 mg/ml) was dissolved in 100% DMSO, and added to DLPC dissolved in tertiary butanol (40° C.) so the final DMSO concentration did not exceed 5 percent of the total volume and the ratio of drug to lipid was 1:50 (w/w). The final suspension was clear. If precipitation occurred, it was reheated to 50–60° C. The preparation was frozen in liquid nitrogen and lyophilized overnight. For use the material was dissolved in sterile water to the appropriate drug concentration, not exceeding 1.0 mg/ml for either drug. The efficiency of incorporation of drug in the liposomes was examined qualitatively by microscopic examination under polarized light. Unincorporated drug was seen as bi-refringent crystals. The efficiency of incorporation was examined by centrifugation of aqueous suspensions of liposomes on Percoll™ gradients. One-tenth ml of suspension was layered over 2 ml of gradient and centrifuged at 2000 rpm for 25–30 minutes. Liposomes layer at the water-Percoll interface, while unincorporated drug was deposited at the bottom of the tube. Many other lipids may be substituted for DLPC in the formulation and use of liposomes for delivery of drugs by aerosol (Sugarman, S. M., et. al. Lipid-complexed campothecin: formulation and initial biodistribution and anti-tumor activity studies. *Cancer Chemotherapy Pharmacol.* 1996 37:531–538).

EXAMPLE 9

HPLC Analysis

The Waters (Milford, Mass.) 710B Wisp automatic injector and Waters Nova-Pak C18 column at room temperature was used to quantitate CPT and 9-NC. The mobile phase was 30% acetonitrile and 70% of 0.1% glacial acetic acid. CPT was detected using the Waters 470 scanning fluorescence detector set to an excitation wavelength of 370 nm and an emission wavelength of 440 nm. 9-NC was detected using the Waters 440 absorbence detector and monitoring at 254 nm. The data were analyzed with the Waters Millenium software.

EXAMPLE 10

Aerosol Droplet Measurement

The size of aerosol droplets was measured with the Andersen ACFM non-viable ambient particle sizing sampler (Andersen Instruments, Inc., Atlanta, Ga.) by methods previously described (Waldrep, J. C. et. al., *J Aerosol Med.* 1994 7:135–145). Mass median aerodynamic diameters and geometric standard deviations were determined using Kaleida-Graph 2.0 (Synergy Software, Reading Pa.). The aerosol droplets consisted of an aqueous suspension of liposomes. Liposome diameters were measured in aqueous suspension with the Model 3300 NICOMP Laser Particle Sizer.

EXAMPLE 11

Preparation and Efficiency of Taxol-DLPC Liposomes Formulated by Aerosol Delivery Taxol is another anti-cancer drug that is lipid soluble and is incorporated easily into liposomal formulation. Taxol is dissolved directly in t-butanol without use of DMSO similar to the camptothecins. The taxol liposomal preparation is otherwise like that of the camptothecins.

The optimal taxol to DLPC ratio was found to be about 1:30 wt:wt. Formulations compatible with nebulization and aerosol delivery formulations were produced at 1 mg Taxol and with 30 mg DLPC per ml. For optimized Taxol-DLPC liposomes, 5 mg of Taxol was mixed with 150 mg of synthetic alpha-lecithin: dilauroylphosphatidylcholine (DLPC). Working at 37° C., the drug/DLPC was mixed in 20 mls of tertiary butanol with stirring. After mixing, the drug/lipid preparation was pipetted into glass vials, frozen rapidly, and lyophilized overnight to remove the t-butanol leaving a powder. Multi-lamellar liposomes were produced by adding 5 mls of ultra pure water above the DLPC phase transition temperature (Tc) at 25° C. to deliver a final standard drug concentration of 1 mg Taxol: 30 mg DLPC per ml. The mixture was incubated for 30 minutes at room temperature with intermittent mixing to produce multilamellar vesicular (MLV) liposomes. Aliquots were removed for determination of drug concentration by HPLC.

Figure 5:
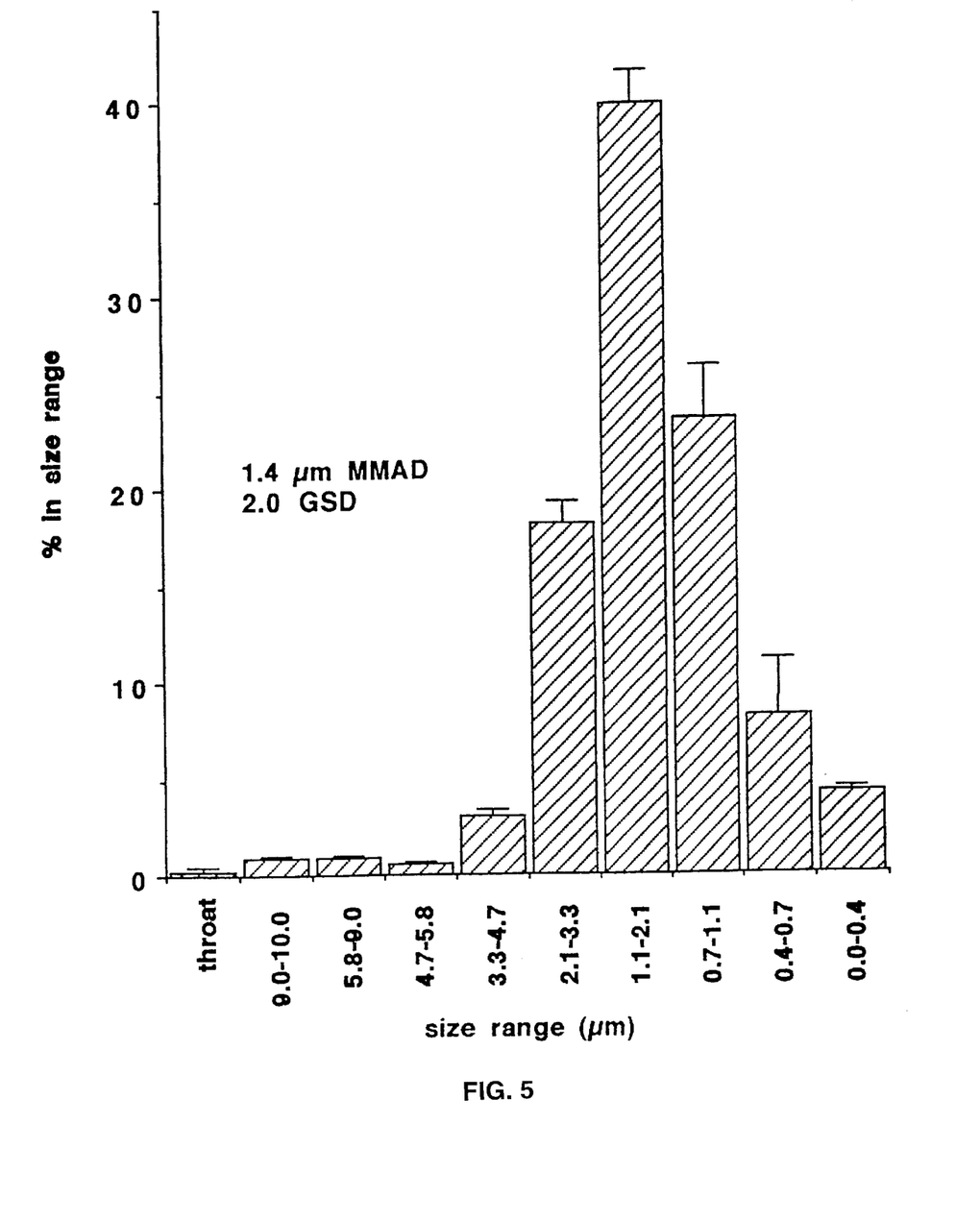
FIG. 5: shows the output of Taxol-DLPC liposomes (1:30; 1 mg/ml) with the Aerotech II nebulizer.
Figure 6:
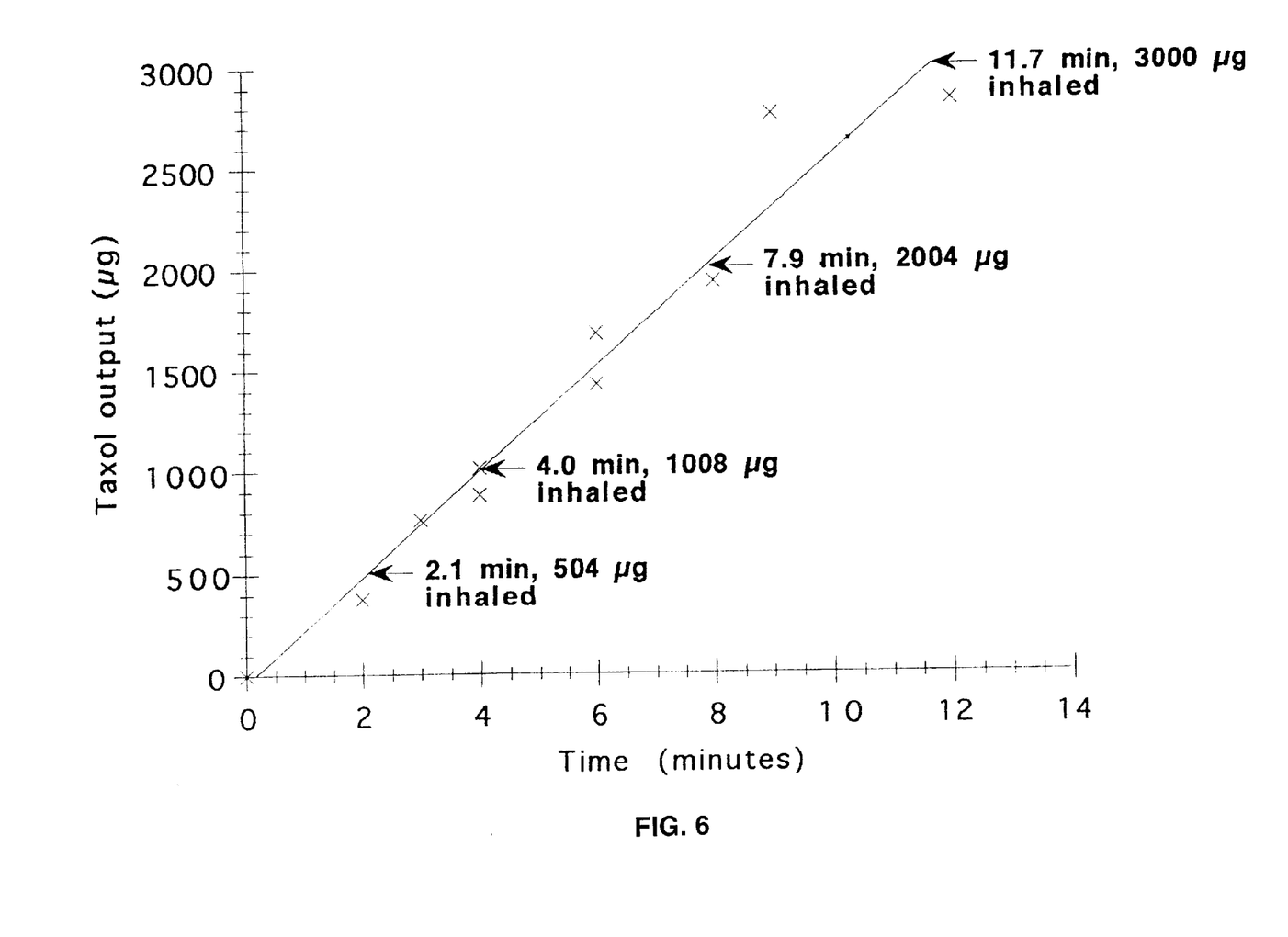
FIG. 6: shows the recovery of taxol from the preparation described in FIG. 5; taxol-DLPC dosage at 15 bpm, 500 ml TV.

FIG. 5 shows the particle size distribution of taxol-DLPC liposome aerosol with a MMAD of 1.4 µm and a geometric standard deviation of 2.0 FIG. 6 shows the recovery of taxol from the preparation described in FIG. 5. In the lung model (Harvard Respirator) used to measure the output of taxol from the nebulizer (Aerotech II), 87.75 liters of aerosol were sampled yielding 3000 µg of taxol. There was thus an aerosol concentration of 34.2 µg/l. From this information, the dose of aerosol deposited in the respiratory tract following inhalation can be calculated.

Any patents or publications mentioned in this specification are indicative of the levels of those skilled in the art to which the invention pertains. Further, these patents and publications are incorporated by reference herein to the same extent as if each individual publication was specifically and individually indicated to be incorporated by reference.

One skilled in the art will appreciate readily that the present invention is well adapted to carry out the objects and obtain the ends and advantages mentioned, as well as those objects, ends and advantages inherent herein. The present examples, along with the methods, procedures, treatments, molecules, and specific compounds described herein are presently representative of preferred embodiments, are exemplary, and are not intended as limitations on the scope of the invention. Changes therein and other uses will occur to those skilled in the art which are encompassed within the spirit of the invention as defined by the scope of the claims.

What is claimed is:

1. A lipsome for delivery of an aqueous dispersion of an anti-cancer drug via small particle aerosol, said liposome comprising the anti-cancer drug, said anti-cancer drug selected from the group consisting of taxol and taxol-A; and a lipid suitable for solubilization and delivery of the anti-cancer drug via said small particle aerosol, wherein the ratio of said anti-cancer drug to lipid is about 1:1 to about 1:2000 wt:wt and wherein the final concentration of said anti-cancer drug in said liposome is no greater than 5.0 mg/ml.

2. The liposome of claim 1 produced by the steps comprising:

dissolving said anticancer drug in an appropriate solvent to produce dissolved anticancer drug;

dissolving said lipid in an appropriate solvent to produce dissolved lipid;

combining said dissolved anticancer drug and said dissolved lipid to produce a solution, wherein said dissolved anticancer drug is at a concentration not exceeding about 10% of the total volume of said solution; and evaporating said solvents from said solution to produce a powder.

3. The liposome of claim 1, wherein said ratio of anti-cancer drug to lipid is about 1:10 to about 1:100 wt:wt.

4. The lipsome of claim 1, wherein said ratio of anti-cancer drug to lipid is about 1:10 to about 1: 50 wt:wt.

5. The lipsome of claim 1, wherein said lipid is dilauroylphosphatidylcholine and said ratio of anti-cancer drug to lipid is about 1:25 to about 1:40 wt:wt.

* * * * *

UNITED STATES PATENT AND TRADEMARK OFFICE
CERTIFICATE OF CORRECTION

PATENT NO.    : 6,346,233 B1                                                      Page 1 of 1
DATED         : February 12, 2002
INVENTOR(S)   : J. Vernon Knight, J. Clifford Waldrep, Nadezhda Koshkina and Brian Gilbert It is certified that error appears in the above-identified patent and that said Letters Patent is hereby corrected as shown below:

Column 1,
Line 57, "is" should read -- are --.
Line 62, "a" should read -- an --.

Column 3,
Line 27, "solutions" should read -- solution --.
Line 40, "Tthe" should read -- The --.

Column 4,
Line 43, please insert the word -- be -- between the words "to" and "interpreted".

Column 5,
Line 11, "terms" should read -- term --.

Column 12,
Line 4, "are" should read -- is --.

Signed and Sealed this

Fifth Day of November, 2002

Attest:

*Attesting Officer*

JAMES E. ROGAN
*Director of the United States Patent and Trademark Office*